United States Patent [19]

Cumbo

[11] 3,950,506

[45] Apr. 13, 1976

[54] PROCESS FOR THE PREPARATION OF AN OLATED CHROMIUM (III) NITRATE

[76] Inventor: Charles C. Cumbo, 1410 Bucknell Road, Green Acres, Wilmington, Del. 19803

[22] Filed: July 9, 1973

[21] Appl. No.: 377,570

Related U.S. Application Data

[63] Continuation-in-part of Ser. No. 119,842, March 1, 1971, abandoned.

[52] U.S. Cl............ 423/607; 260/438.5 C; 423/387
[51] Int. Cl.$^2$......................................... C01B 37/02
[58] Field of Search ............ 423/387, 607; 260/438

[56] References Cited
UNITED STATES PATENTS
2,544,668   3/1951   Goebel et al................. 260/438.5 C FOREIGN PATENTS OR APPLICATIONS
879,385   6/1956   Germany............................ 423/395

OTHER PUBLICATIONS

Hall et al., "Journal of the American Chemical Society", Vol. 72, pp. 782–790, (1956).

"Chemical Abstracts", Vol. 55, 1961, pp. 18150–18151.

Primary Examiner—G. O. Peters

[57] ABSTRACT

Olated chromium (III) nitrate is obtained by dissolving hexaaquochromium (III) nitrate in a $C_1$–$C_4$ alcohol or in tetrahydrofuran, any of them containing less than about 10% of water. The preferred alcohol is isopropyl alcohol. The preparation can also start with chromium trioxide, which is reduced to chromium (III) nitrate by a reducing alcohol, such as isopropyl alcohol, in the presence of nitric acid. Alternatively, the reduction can be accomplished in a nonreducing organic solvent such as tetrahydrofuran, by hydrogen peroxide in the presence of nitric acid. Highly olated chromium nitrate is an excellent coupling agent for reinforced thermoplastic composites. Olation in the presence of a carboxylic acid or addition of a carboxylic acid to the olated chromium (III) nitrate gives carboxylic acid-olated chromium (III) nitrate complexes, which are useful as coupling agents or as mold release agents.

2 Claims, No Drawings

PROCESS FOR THE PREPARATION OF AN OLATED CHROMIUM (III) NITRATE

CROSS REFERENCE TO RELATED APPLICATION

This application is a continuation-in-part of application Ser. No. 119,842, filed Mar. 1, 1971 now abandoned, and assigned to the same assignee as the present application.

BACKGROUND OF THE INVENTION

This invention relates to a process for the preparation of olated chromium (III) complexes and to certain novel complexes prepared thereby.

Formation of fumarato chromium (III) nitrate complexes from chromium (III) hexaaquo nitrate has been disclosed in the applications of A. J. Deyrup, Ser. Nos. 25,097, filed Apr. 2, 1970 and now abandoned, 119,608, filed Mar. 1, 1971, and 210,833, filed Dec. 22, 1971, all assigned to the assignee of the present application. It is recognized in the Deyrup applications that dimeric or polymeric complexes can be formed in the process of his invention, which involves repeated boiling in water of fumaric acid and hexaaquo chromium nitrate, together with a careful pH adjustment at each stage. While dimeric or polymeric complexes undoubtedly are formed in that process, the technique is lengthy and cumbersome. The chromium complexes prepared by Deyrup are useful agents for coupling glass, metals, or metal oxides to resins.

Dimerization of chromic salts by boiling in aqueous solutions is explained by Stiasny ("Gerbereichemie", Steinkopff, Dresden, 1931) as resulting from "olation", as follows:

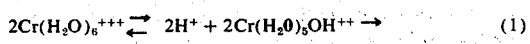  (1)

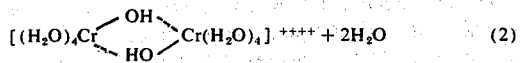  (2)

Hall and Eyring (J. Am. Chem. Soc. 72, 782-90, 1956) observed that the formation of oxygen bridges is facilitated by addition of ethanol to a solution of chromic nitrate before refluxing. Hall and Eyring favor formulas such as (3) or (4), below, for the plated chromium compounds:

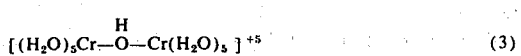  (3)

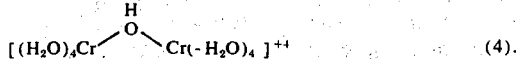  (4)

Although the above authors studied quite thoroughly the kinetics of olation, their standard procedure involved refluxing aqueous chromic salt solutions for 60 hours to obtain the maximum number of oxygen bridges. In some cases, Hall and Eyring refluxed chromic salt solutions in 90% ethanol and noticed a change in color as well as increase in acidity after only a few minutes. Rollinson observes in Bailar "Chemistry of the Coordination Compounds", 1956, p. 458, that Hall and Eyring's paper suggests that the alcohol competes with chromium for the hydroxo groups as well as the aquo groups, thereby leading to the loss of protons from the ol bridges and the formation of oxo bridges. This is oxolation at the expense of olation.

It can be shown that at room temperature, only a very small amount of olation occurs in a solution containing even as little as 10% of water. Moreover, at elevated temperatures, e.g. at reflux, undersired reactions, such as reduction of the nitrate by the alcohol, can occur. It is, therefore, undesirable to prepare olated chromium (III) nitrate complexes under the conditions used by Hall and Eyring.

SUMMARY OF THE INVENTION

According to this invention, it has now been found that olated chromium (III) nitrate complexes, which are useful in their own right as coupling agents for borosilicate glass fiber-thermoplastic resin composites, are formed readily at 0°–50°C. in at least one solvent from the group: alcohol having 1–4 carbon atoms and tetrahydrofuran, containing less than about 10% of water. When the amount of water is sufficiently small or the temperature is close to 50°C., complexes having a degree of olation of more than 50% are obtained. Such complexes are considered to be highly olated. For the purposes of the present invention, the degree of olation is defined in the following manner: When one equivalent of acid is liberated in the olation process during the step of formation of the basic chromium nitrate intermediate (1) per atom of chromium, olation is considered complete; the degree of olation is 100%. A degree of olation of more than 50% means that more than 0.5 acid equivalent per atom of chromium is liberated during the first step. It is assumed that the basic intermediate (1) olates completely to (2) or similar compounds.

Instead of using hexaaquo chromium nitrate as the starting material, it is possible to start with chromium trioxide, which first is reduced in the substantially nonaqueous medium in the presence of nitric acid to chromium (III) nitrate. The nonaqueous medium can be a reducing alcohol of 1–4 carbon atoms, in which case it can itself serve as the reducing agent. The solvent can be tetrahydrofuran or a nonreducing alcohol, but hydrogen peroxide or another reducing agent must be added. Olation also can be carried out in the presence of carboxylic acids, with formation of olated chromium nitrate complexes with such acids.

DETAILED DESCRIPTION OF THE INVENTION

Alcohols having 1–4 carbon atoms and tetrahydrofuran are effective because they are very good solvents for chromium nitrate and because olation proceeds very rapidly in these solvents and reaches a much greater degree than it does in water. Other solvents, such as methyl ethyl ketone, acetone, and dioxane, also may be present, but $C_1$–$C_4$ aliphatic alcohols and/or tetrahydrofuran should preferably constitute more than 50 weight percent of the final reaction mixture. In the preferred process, chromium trioxide is used as the starting material, and it must first be reduced to chromium (III) nitrate.

Many organic reducing compounds, such as alcohols, aldehydes, or sugars can be used in this process but secondary aliphatic alcohols are preferred. This is so because secondary alcohols are oxidized to ketones, which do not intefere with most applications of the products. Excess alcohol serves, of course, as the reaction medium. Primary alcohols are less suitable because they are oxidized to aldehydes, which impart undesirable odor; while aldehydes are oxidized to carboxylic acids, which tend to form complexes with chromium (III) nitrate. In some cases it is desirable, however, to use a primary alcohol as part of the reducing agent. The alcohol is then so chosen that the proper aldehyde and then the corresponding carboxylic acid is formed, the latter forming a chromium complex. Isopropyl alcohol, tert-butyl alcohol, isobutyl alcohol, and tetrahydrofuran are greatly superior to methanol and somewhat superior to ethanol as the reducing compound for use in the invention in terms of speed of the reaction.

Reduction of chromium trioxide by isopropyl alcohol is shown in the following equation:

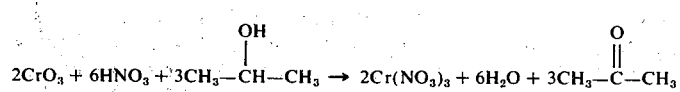

The secondary alcohols which can be used in the preferred process of this invention are isopropyl alcohol and sec-butyl alcohol, the former being particularly suitable because of its low price and low molecular weight. The normal alcohols are methanol, ethanol, n-propanol, and n-butanol. Tertiary butyl alcohol is not a reducing agent in the process of the present invention but it can be used as a solvent in the presence of a reducing agent. Tetrahydrofuran is the preferred solvent because olation proceeds in this medium even further than in isopropyl alcohol. The preferred reducing agent in substantially nonaqueous tetrahydrofuran is hydrogen peroxide, which reacts according to the following equation:

When hydrogen peroxide is used, no ketones or other organic impurities are formed.

Although chromium trioxide is the most economical and practical starting material in the process of this invention, olation can start with commercial chromium (III) nitrate, and the reduction step is then eliminated. The main disadvantage of hydrated chromium nitrate is its relatively high cost and lack of batch-to-batch uniformity of the chromium level in the commercial material. Other chromium compounds are less practical because they may introduce undesirable ions which would interfere either with olation or with subsequent use of the olated material.

In order to obtain chromium (III) nitrate by reduction of chromium trioxide, it is necessary to add nitric acid to the reduction medium. Ordinarily, 2 to 3 moles of nitric acid per mole of chromium trioxide are used. Larger amounts of nitric acid are undesirable because excess acid may shift the olation equilibrium to the left.

An olated chromium nitrate can be, if desired, further combined with a carboxylic acid to form a complex. Virtually any carboxylic acid can thus be added to the reaction medium and can be expected to complex with the chromium atom. Certain complexes have outstanding properties as coupling agents for mineral fillers and reinforcing agents useful in forming composites with thermosetting or thermoplastic resins. Certain complexes with long chain acids are useful mold release agents. Representative carboxylic acids include, for instance, fumaric, mesaconic, aconitic, terephthalic, p-phenoxyacetic, methacrylic, stearic, palmitic, cinnamic, succinic, acrylic, acetylenedicarboxylic, maleic, adipic and myristic acids; as well as monoesters of dicarboxylic acids, such as monoethyl fumarate, monomethyl mesaconate, and monoethyl terephthalate.

In the preferred process of this invention, a concentrated solution of $CrO_3$ in water (about 28 weight percent $CrO_3$) is slowly added to isopropyl alcohol containing 2–3 moles of nitric acid per mole of $CrO_3$, at a temperature of 0°–50°C., preferably below 35°C. The amount of isopropyl alcohol is such that the resulting aqueous isopropyl alcohol solution contains less than about 10 weight percent of water. If a carboxylic acid complex is desired, the appropriate carboxylic acid is then added. Normally, an amount of the carboxylic acid equimolar with chromium trioxide will be used. Greater or lesser amounts can be used but are less desirable for most applications. It sometimes is practical to add as the last step up to one equivalent of an alkali per mole of $CrO_3$. This alkali neutralizes free nitric acid formed in the first step of olation and allows olation to proceed further. An excess of nitric acid also is undesirable because it could cause conversion of the olated structure to the monomeric chromium (III) nitrate. The $CrO_3$ solution can also be added simultaneously with the reducing alcohol to a heel, but addition of the alcohol to the $CrO_3$ solution should be avoided because the reaction is very exothermic in the presence of an excess of $CrO_3$.

It should be kept in mind that addition of solid chromium trioxide to anhydrous isopropyl alcohol, or to any other anhydrous organic compound is dangerous and should not be attempted. Chromium trioxide is a powerful oxidizing agent, and it can easily ignite an organic compound, especially an organic reducing agent.

Whether starting with $CrO_3$ or with $Cr(NO_3)_3$, olated chromium nitrate is formed in a substantially nonaqueous medium very quickly. Heating normally is not required, as the reaction proceeds spontaneously at room temperature. At the upper limit of the water content, close to about 10%, heating for a short time at 50°C. may be worthwhile. The progress of the olation reaction can be conveniently followed by known analytical techniques, e.g. by pH determination and by conductometric titration. The first step is accompanied by a decrease of the solution pH, apparently due to the displacement of a proton from the olating water molecule. This increase in the proton concentration also results in an increase in the conductivity of the solution. The following reactions are believed to be taking place in the presence of a sufficient quantity of water:

$$Cr(H_2O)_6{}^{+3} \rightleftharpoons [Cr(H_2O)_5OH]^{+2} + H^+$$

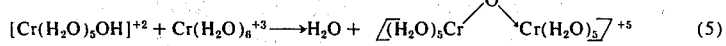

$$[Cr(H_2O)_5OH]^{+2} + Cr(H_2O)_6{}^{+3} \longrightarrow H_2O + [(H_2O)_5Cr\overset{H}{\underset{O}{\diagup\diagdown}}Cr(H_2O)_5]^{+5} \quad (5)$$

The formation of olated chromium (III) nitrate (5) in the second step is not accompanied by changes in acidity, but it can be followed by spectroscopy in the visible region. Both the wavelengths of the absorption maxima and the molar extinction coefficients change as the olation progresses. This phenomenon was observed by Laswick and Plane, J. Am. Chem. Soc. 81, 3566 (1959) in the case of olated chromium perchlorate. In the present case, it has been found that the spectra of aqueous monomeric chromium nitrate, basic chromium nitrate, and olated chromium nitrate differ as follows:

| Chromium Nitrate | First maximum | | Second maximum | |
|---|---|---|---|---|
| | $\lambda_1$ | $\epsilon_1{}^*$ | $\lambda_2$ | $\epsilon_2{}^*$ |
| Monomeric | 4092 | 16.0 | 5750 | 14.0 |
| Basic | 4311 | 26.0 | 5880 | 14.0 |
| Olated | 4147 | 22.0 | 5780 | 17.2 |

*Calculated as if all chromium were present in the form of monomeric chromium (III) nitrate.

Further olation reactions may occur to give multiple bridges and higher polymers, such as

(6)

(7)

(8)

where for simplicity, the coordinated water molecules are not represented; but it is to be understood that each Cr is coordinated with a total of six groups. One or more water molecules may be replaced by another solvent or by a carboxylic acid, for example.

It should be kept in mind that the preparation of carboxylic acid complexes does not necessarily require a separate step for the introduction of the carboxylic acid into the reaction medium. It is entirely possible to have the carboxylic acid present in the medium even before chromic nitrate or chromium trioxide is introduced thereto. When it is desired, however, to follow the progress of olation by either pH or conductivity determination, the presence of the carboxylic acid is undesirable at an early stage.

The process of this invention can be operated within the temperature range of 0°–50°C. The olation is too slow to be practical below 0°C., while above 50°C. undesirable side reactions become significant. Furthermore, in some instances, excessive olation can occur above 50°C., resulting in reduced solubility and poorer performance characteristics.

The most practical temperature range is 25°–50°C. since work in the 0°–25°C. range normally would require expensive refrigeration.

This invention is now illustrated by certain representative embodiments thereof, wherein all parts, proportions and percentages are by weight unless otherwise indicated.

EXAMPLE 1

Preparation of Olated Chromium Nitrate in Ethanol

Chromium (III) nitrate nonahydrate (8.0 g., 0.02 mole) is dissolved in 100 ml. of anhydrous ethanol, producing a blueviolet solution. The olation reaction is allowed to proceed for 170 minutes at room temperature (+25°C.). At the end of this time, the color of the solution is dark green. The progress of the reaction is monitored by periodically removing 3 ml. aliquots, diluting them to 25 ml. with water and determining their hydrogen ion concentration. The results are presented below in Table I.

TABLE I

| Time (min.) | pH |
|---|---|
| 10 | 2.70 |
| 30 | 2.25 |
| 50 | 2.15 |
| 90 | 1.95 |
| 170 | 1.90 (equilibrium value) |

Examination of the visible spectrum of the olated chromium (III) nitrate in water on a Cary Model 11 spectrophotometer at a scanning rate of 30 m$\mu$ per minute gives the following results:

$\lambda_1$ 415 m$\mu$   $\epsilon_1$ 22.5
$\lambda_2$ 578 m$\mu$   $\epsilon_2$ 17.9

The molar extinction coefficients $\epsilon_1$ and $\epsilon_2$ are calculated as if all chromium were in the form of monomeric chromium nitrate. Conductimetric titration of the reaction mixture shows that 0.56 proton equivalent is liberated per equivalent of chromium (III). By comparison, in 90% ethanol only 0.068 proton equivalent is liberated at room temperature in 170 minutes.

For conductimetric titration, 50 ml. of the olated chromium nitrate solution is dissolved in 500 ml. of water and titrated with 1.0 M sodium hydroxide. The conductance of the solution is recorded after each 1.0 ml. base addition. The end point is determined by plotting the conductance versus ml. of 1.0 M NaOH. The point at which the slope of the graph changes abruptly is the end point. Blank runs show that this method is very accurate for the determination of nitric acid in the presence of chromium (III) nitrates.

In contrast to these results, chromium (III) nitrate in water does not olate at 25°C., as evidenced by the constant pH of the solution. The value of the pH, determined for the same aliquot concentration as above, is given below:

TABLE II

| Time (days) | pH |
|---|---|
| 1 | 2.90 |
| 2 | 3.00 |
| 3 | 3.00 |

Olation does occur upon refluxing the aqueous solution, but pH measurements show that the equilibrium mixture liberates only 0.28 proton equivalent per equivalent of chromium (III).

EXAMPLE 2

Preparation of Olated Chromium Nitrate in Tetrahydrofuran

The procedure of Example 1 is repeated using 100 ml. of anhydrous tetrahydrofuran in place of ethanol and identical aliquots are removed for the pH determination. It can be seen from Table III that equilibrium is reached sooner, and that olation is more complete in tetrahydrofuran than in alcohol.

TABLE III

| Time (min.) | pH |
|---|---|
| 0 | 2.90 |
| 10 | 2.10 |
| 25 | 1.75 |
| 40 | 1.69 |
| 110 | 1.69 (equilibrium value) |

Examination of the visible spectrum of the olated chromium (III) in water gives the following results:

$\lambda_1$ 418 m$\mu$, $\epsilon_1$ 25.4
$\lambda_2$ 580 m$\mu$, $\epsilon_2$ 17.5

Conductimetric titration of the reaction mixture shows that 1.0 equivalent of nitric acid is liberated per equivalent of chromium (III).

EXAMPLE 3

Formation of an Olated Fumarato Chromium(III) Nitrate

The procedure of Example 1 is repeated, followed by the addition of 0.02 mole of fumaric acid at the end of 170 minutes. The acid reacts rapidly, producing a dark-blue solution. Conductimetric titration of liberated nitric acid shows that 70% of the fumaric acid has reacted. The reaction is completed by the addition of 0.02 mole of sodium ethoxide (20 ml. of a 1.0 N solution). Examination of the visible spectrum in an aqueous solution of the 70% reaction and 100% reaction products gives the following results:

70% fumaric acid reacted
$\lambda_1$ 411 m$\mu$, $\epsilon_1$ 25.4
$\lambda_2$ 573 m$\mu$, $\epsilon_2$ 28.8
100% fumaric acid reacted
$\lambda_1$ 411 m$\mu$, $\epsilon_1$ 29.0
$\lambda_2$ 573 m$\mu$, $\epsilon_2$ 32.0

Either one of the above complexes, when used as a coupling agent gives borosilicate glass fiber-polyethylene composites with high flexural strength and resistance to moisture. Such composites can be formed, for example, by dipping borosilicate glass fibers in a solution of the complex containing 0.05–0.2% chromium, allowing to dry, making a multilayer structure of alternate layers of treated glass-fiber fabric and polyethylene powder and pressing the structure at about 860 psi and 175°C. during a period of about 2 minutes.

The above procedure is used with the following carboxylic acids, and the corresponding carboxylic acid complexes of olated chromium (III) nitrate are obtained:

Example 4 — Succinic acid
Example 5 — Adipic acid
Example 6 — Mesaconic acid
Example 7 — Maleic acid
Example 8 — Acetylenedicarboxylic acid
Example 9 — Aconitic acid
Example 10 — Phenoxyacetic acid
Example 11 — Myristic acid
Example 12 — Stearic acid
Example 13 — Methacrylic acid

EXAMPLE 14

A complex of olated chromium (III) nitrate and terephthalic acid is made by dissolving 8.0 g. of chromium (III) nitrate nonahydrate in 500 ml. of anhydrous ethanol, followed by the addition of 0.02 mole of terephthalic acid at the end of 170 minutes.

EXAMPLE 15

Preparation of Olated Chromium Nitrate from Chromium Trioxide in Isopropyl Alcohol A solution of 2.0 grams of chromium trioxide (0.02 mole $CrO_3$) in 5.0 ml of distilled water is added slowly and with stirring to a solution of 3.8 ml. of 15.7 N $HNO_3$ (0.06 mole) in 100 ml. of isopropyl alcohol. The addition requires 70 minutes, by which time the temperature of the solution has increased to 35°C. The reaction is allowed to proceed for 3.0 hours. At the end of this time, an aliquot dissolved in water gives the following visible spectrum:

$\lambda_1$ 415 m$\mu$, $\epsilon_1$ 22.5
$\lambda_2$ 580 m$\mu$, $\epsilon_2$ 15.8

EXAMPLE 16

Preparation of an Olated Fumarato Chromium (III) Nitrate

The process of Example 15 is repeated, followed by the addition of 0.02 mole of fumaric acid at the end of 3.0 hours. The acid reacts rapidly, producing a dark-blue solution. Conductimetric titration shows that 70% of the fumaric acid has reacted. Complete reaction of the fumaric acid is accomplished by the addition of 0.02 mole of sodium ethoxide (20 cc. of 1.0 N solution). Spectral data are similar to those of Example 3.

The complexes of Examples 4–13 can also be prepared by the process of Example 16 by substituting the appropriate acid for fumaric acid.

EXAMPLE 17

Reduction of $CrO_3$ with Hydrogen Peroxide

A solution of 2.0 grams of chromium trioxide (0.02 mole $CrO_3$) in 5.0 ml. of distilled water is added slowly and with stirring to a solution of 3.8 ml. 15.7 N $HNO_3$ (0.06 mole) and 3.4 grams of aqueous 30% hydrogen peroxide in 100 ml. of anhydrous tetrahydrofuran. A similar product to that of Example 15 is obtained.

EXAMPLE 18

Laminate Preparation

Eight grams of commercial $Cr(NO_3)_3.9H_2O$ is dissolved in 50 ml. of anhydrous ethanol and allowed to stand overnight at room temperature to form olated chromium (III) nitrate. The solution is diluted with distilled water to 1 liter, and its pH is adjusted to 3 with aqueous NaHCO₃. This solution, containing 0.1% of chromium, is used as a coupling agent for a type "E" borosilicate glass fabric. The commercial fabric is dipped in this solution and dried without rinsing.

A structure of alternate layers of the treated glass fabric and of polyethylene powder (Alathon 7050) is prepared and pressed at 175°C. and 830 psi for 2 minutes. The resulting laminate, which contains about 64 weight percent glass, has a flexural strength of the order of 38,000 psi which retains 87% of its original value after boiling in water for 2 hours.

EXAMPLE 19

Paper Waterproofing

A stearato complex of olated chromium (III) nitrate is prepared as in Example 12. One part of this complex is diluted with 12 parts of water. One-half of a piece of laboratory filter paper is treated with this solution and dried at 150°C. The paper is held at a 45° angle and water is dropped onto both the treated and untreated halves. The water soaks into the untreated half quickly, while most of the water runs off the treated portion with little or no penetration.

EXAMPLE 20

The ability of various solvents to influence the rate and extent of olation of chromium (III) nitrate is illustrated by a series of experiments in which chromium (III) nitrate was dissolved at about 25°C. in methanol, ethanol, isopropanol and tert-butyl alcohol, and the pH was measured after various periods of time. The pH is an effective measure of the extent of olation, since olation produces hydrogen ions resulting in a decrease in the pH as the amount of olated material increases. The results of these tests are presented in Table III below:

TABLE III

Effect of Structure of Alcohol on Olation

| MeOH | | EtOH | | i-PrOH | | t-BuOH | |
|---|---|---|---|---|---|---|---|
| T(min) | pH | T(min) | pH | T(min) | pH | T(min) | pH |
| 10 | 2.86 | 10 | 2.70 | 10 | 2.51 | 35 | 1.80 |
| 30 | 2.80 | 30 | 2.25 | 30 | 2.11 | 90 | 1.63 |
| 50 | 2.80 | 50 | 2.15 | 50 | 1.93 | | |
| 90 | 2.72 | 90 | 1.95 | 90 | 1.80 | | |
| 170 | 2.67 | 170 | 1.90 | 170 | 1.70 | | |

These results show that isopropanol and tert-butyl alcohol cause olation more rapidly and to a greater extent than do either ethanol or methanol.

I claim:

1. A process for preparing an olated chromium (III) nitrate, said process comprising admixing at 0°–50°C. a concentrated aqueous solution of chromium trioxide with a reducing alcohol selected from isopropyl alcohol and isobutyl alcohol containing about 3 moles of nitric acid per mole of said chromium trioxide, the amount of said alcohol being such that less than about 10 weight percent of water is present in the reaction mixture; and maintaining all the reaction components in contact at 0°–50°C. until olation has substantially reached equilibrium conditions;

provided there never is present in the reaction mixture an excess of chromium trioxide.

2. A process of claim 1 wherein the temperature is maintained at 25°–50°C.

* * * * *